United States Patent [19]

Russell

[11] Patent Number: 4,874,771
[45] Date of Patent: Oct. 17, 1989

[54] ETHANESULFONAMIDE DERIVATIVES

[75] Inventor: Ronald K. Russell, Titusville, N.J.

[73] Assignee: Ortho Pharmaceutical Corporation, Raritan, N.J.

[21] Appl. No.: 240,976

[22] Filed: Sep. 6, 1988

[51] Int. Cl.$^4$ .............. A61K 31/445; A61K 31/495; C07D 211/18; C07D 295/08
[52] U.S. Cl. .................................. 514/331; 546/232; 546/233; 544/398; 544/399; 544/400; 544/159; 548/578; 540/484; 514/255; 514/237.5; 514/408; 514/213

[58] Field of Search ............... 514/331, 255, 239.5, 514/408, 213; 544/398, 399, 400, 159; 546/232, 233; 548/578; 540/484

[56] References Cited

U.S. PATENT DOCUMENTS 4,293,557 10/1981 Shibata et al. ............... 514/331

Primary Examiner—Richard L. Raymond
Assistant Examiner—Mark W. Russell
Attorney, Agent, or Firm—Benjamin F. Lambert

[57] ABSTRACT

The synthesis of novel ethanesulfonamide compounds is described. The novel ethanesulfonamide compounds have antisecretory activity and are used in the treatment of peptic ulcer disease.

7 Claims, No Drawings

ETHANESULFONAMIDE DERIVATIVES

BACKGROUND OF THE INVENTION

The present invention relates to novel ethanesulfonamide derivatives in which the sulfonamide moiety is bonded to a 3-(cycloalkylaminomethyl)phenoxyalkylamine. The ethanesulfonamide derivatives are useful as anti-secretory agents which can be used in the treatment of peptic ulcer disease.

SUMMARY OF THE INVENTION

The present invention is directed to ethanesulfonamide compounds of the formula

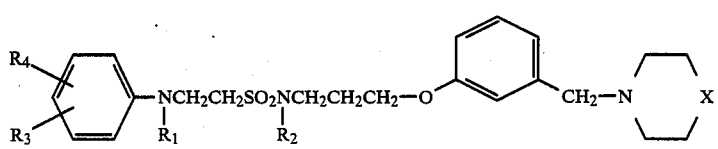

I where
R$_1$ may be hydrogen or C$_1$-C$_3$ alkyl;
R$_2$ may be hydrogen or a pharmaceutically acceptable alkali or alkaline earth metal ion such as sodium, potassium, calcium or magnesium;
R$_3$ may be hydrogen, Cl, Br, F, C$_1$-C$_6$ alkyl, C$_3$-C$_6$ branched-chain alkyl, C$_1$-C$_6$ alkoxy, C$_3$-C$_6$ branched-chain alkoxy, CF$_3$, nitro, —NHCOC$_1$-C$_3$ alkyl, NR$_5$R$_6$ or CO$_2$R$_7$ when R$_4$ is hydrogen, or R$_3$ and R$_4$ are the same or different and are Cl, Br, F or CF$_3$;
R$_5$ and R$_6$ are the same or different and may be hydrogen or C$_1$-C$_3$ alkyl;
R$_7$ may be hydrogen or C$_1$-C$_6$ alkyl;
X may be O, NR$_8$, CHR$_8$ or —(CH$_2$)$_n$—;
R$_8$ may be C$_1$-C$_3$ alkyl; and
n may be 0, 1, 2 or 3;
and its physiologically acceptable salts.

The compounds of formula I are useful as antisecretory agents which can be used in the treatment of peptic ulcer disease.

No examples of a sulfonamide moiety bonded to a 3-(cycloalkylaminomethyl)phenoxyalkylamine have been found in the literature.

DETAILED DESCRIPTION OF THE INVENTION

The invention in its broadest aspects relates to ethanesulfonamide derivatives which have antisecretory activity in mammals. The ethanesulfonamide compounds of the invention demonstrating antisecretory activity are shown in formula I above.

The preferred compounds of formula I of the present invention are those wherein
R$_1$ and R$_2$ are hydrogen;
R$_3$ is hydrogen, Cl, Br, F, nitro, C$_1$-C$_6$ alkyl, C$_3$-C$_6$ branched-chain alkyl, CF$_3$ or CO$_2$R$_7$, and R$_4$ is hydrogen, or R$_3$ and R$_4$ are each Cl or CF$_3$;
R$_7$ is C$_1$-C$_6$ alkyl;
X is —(CH$_2$)$_n$—; and
n is 1 or 2.

The compounds of formula I are prepared as shown in Scheme I.

SCHEME I

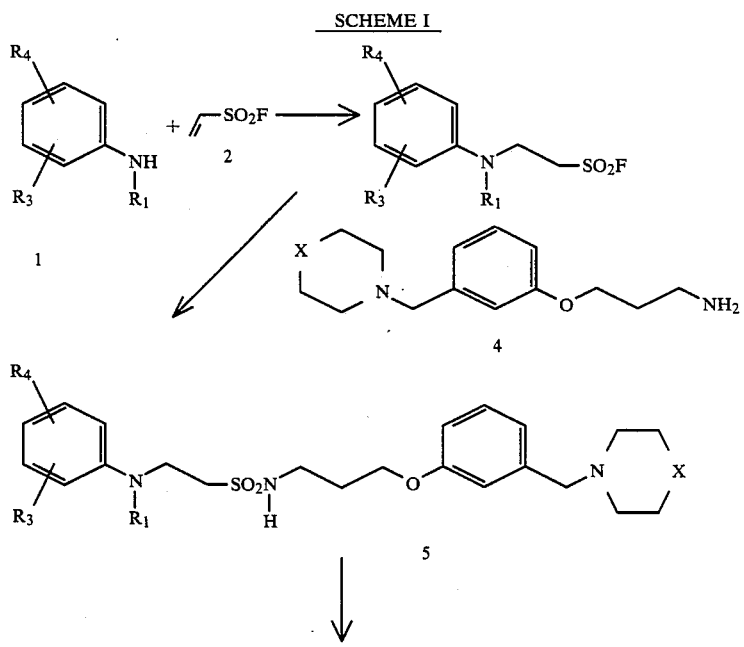

SCHEME I

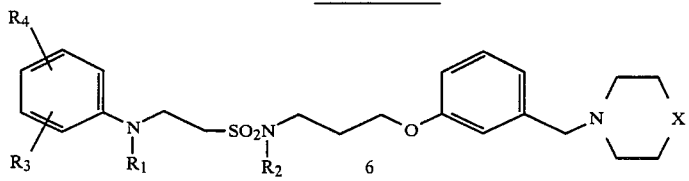

-continued

The compounds of formula I are prepared as follows:

The aniline 1 is obtained as a commercial material or where $R_1$ is lower alkyl, the aniline is prepared by literature procedures such as G. W. Gribble et al., *J. Am. Chem. Soc.* 96, 7812 (1974). The ethenesulfonyl fluoride 2 is obtained as a commercial material or prepared by the literature procedure of J. J. Krutak et al., *J. Org. Chem.* 44, 3847 (1979). The aniline 1 wherein $R_3$ and $R_4$ may represent hydrogen, 4-bromo, 4-fluoro, 3,4-dichloro, 4-butyl, 4-pentoxy, 4-isopropoxy, 4-chloro-3-trifluoromethyl, 4-nitro, 4-acetylamino, 4-ethoxycarbonyl, or 4-methylmercapto or other substituents, is mixed with ethenesulfonyl fluoride in an inert solvent such as toluene, acetic acid, dioxane, or N,N-dimethylformamide at a temperature of about 100°–130° C. for about three to 72 hours to afford the ethanesulfonyl fluoride 3.

The crude sulfonyl fluoride 3 is reacted with the phenoxypropylamines 4, which are known compounds described in the literature, wherein X may be O or $NR_7$ (Merck and Co. European Patent No. 40696), wherein $R_7$ is lower alkyl, or X may be $CHR_7$ or $—(CH_2)_n—$, wherein n may be 0, 1, 2 or 3 (Bristol-Meyers Co., French Patent No. 2505835). The reaction may be done without a solvent or in an inert basic solvent such as triethylamine, pyridine, lutidine, quinoline or 1,8-diazabicyclo[5.4.0]undec-7-ene at about 80° C. to about 120° C. for about 18 to 20 hours. The sulfonamide 5 is obtained as a viscous liquid which may be mixed with a pharmaceutically acceptable acid such as, for example, ethanedioic acid, (E)- or (Z)-2-butenedioic acid, butanedioic acid, or HCl, or other acids, in an inert solvent such as methanol, ethanol, isopropanol, acetone or ether to afford an acid salt of sulfonamide 5 as a solid. The free-base sulfonamide 5 may also be mixed with a base such as, for example, NaOH, KOH, or $Ca(OH)_2$, or other bases, in an inert solvent such as methanol, ethanol or isopropanol to afford sulfonamide 5 after solvent removal as a solid, wherein $R_2$ is a pharmaceutically acceptable alkali or alkaline earth metal ion. The free-base sulfonamide 5, wherein $R_3$ is $NHCOCH_3$, may be treated with one equivalent of NaOH or KOH in an inert solvent such as methanol or ethanol to produce the sulfonamide 5, wherein $R_3$ is $NH_2$.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, parenteral, aerosol or topical. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions) or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 100 to about 2400 mg/kg, and preferably from about 250 to about 800 mg/kg of the active ingredient.

The following examples describe the invention in greater particularity and are intended to be a way of illustrating but not limiting the invention.

EXAMPLE 1

2-[(3,4-Dichlorophenyl)amino]-N-[3-[3-piperidinomethyl)phenoxy]propyl]ethanesulfonamide A N,N-dimethylformamide solution (DMF, 100 ml) of 3,4-dichloroaniline (6.48 g, 40 mmol) and ethenesulfonyl fluoride (6.7 g, 57.9 mmol) was warmed to 110° C. for three hours. The cooled dark solution was diluted to 400 ml with water and the resulting dark oily precipitate was decanted from the supernatant layer. This layer was extracted with ether (4×50 ml). The combined ether extracts were added to the oily precipitate and this dark solution was washed with brine and dried over $MgSO_4$. The organic solution was evaporated to give the crude 2-[(3,4-dichlorophenyl)amino]ethanesulfonyl fluoride as a dark liquid in quantitative yield.

The above product (2.54 g, 9.33 mmol) was mixed with 3-[3-(piperidinomethyl)phenoxy]propylamine (2.6 g, 10.5 mmol) in 10 ml of pyridine. After the solution had been warmed to 100° C. for 18 hours under nitrogen, it was cooled and diluted to 100 ml with $H_2O$. A dark oily precipitate was isolated and dissolved in $CH_2Cl_2$, washed with $H_2O$ and brine and dried over $MgSO_4$. The organic solution was evaporated and the crude product was purified by flash silica gel (200 g) chromatography using 50% EtOAc in hexane and then EtOAc to afford the title compound (1.6 g, 34.3% yield) as a yellow viscous liquid. This material was converted to its monooxalate salt in acetone, mp 112°–120° C.

Theor. $C_{23}H_{31}Cl_2N_3O_3S \cdot C_2H_2O_4$: C, 50.85; H, 5.63; N, 7.12 Found: C, 50.83; H, 5.63; N, 6.97

When in the above procedure, 4-nitroaniline, aniline or N-ethylaniline is used in place of the dichloroaniline, the corresponding (4-nitrophenyl)amino, phenylamino or N-ethylphenylamino derivative is obtained.

EXAMPLE 2

2-[(4-Fluorophenyl)amino]-N-[3-[3-(piperidinomethyl)-phenoxy]propyl]ethanesulfonamide The 2-[(4-fluorophenyl)amino]ethanesulfonyl fluoride was produced following the procedure of Example 1 using 4-fluoroaniline (3.33 g, 30 mmol) and ethenesulfonyl fluoride (3.63 g, 33 mmol).

The title compound was produced following the procedure of Example 1 using the above crude ethanesulfonyl fluoride (6.65 g, 30 mmol) and the amine (8.18 g, 33 mmol) in Example 1. The title compound was isolated as a light yellow-green oil in 21.7% yield (2.93 g) after silica gel (200 g) chromatography and was converted to its monooxalate salt in acetone (softens at 115° C., mp 122°–124° C.).

Theor. $C_{23}H_{32}FN_3O_3S \cdot C_2H_2O_4$: C, 55.65; H, 6.35; N, 7.79 Found: C, 55.50; H, 6.61; N, 7.95

EXAMPLE 3

2-[(4-Ethoxycarbonylphenyl)amino]-N-[3-[3-piperidinomethyl)phenoxy]propyl]ethanesulfonamide The crude 2-[(4-ethoxycarbonylphenyl)amino]ethanesulfonyl fluoride was produced following the procedure of Example 1 using ethyl 4-aminobenzoate (4.96 g, 30 mmol) and ethenesulfonyl fluoride (30 mmol) at 120° C. for 24 hours.

The title compound was produced following the procedure of Example 1 using the above ethanesulfonyl fluoride (6.55 g, 23.8 mmol) and the amine (6.49 g, 26.2 mmol) in Example 1. The title compound was purified by silica gel (200 g) chromatography and converted to its monooxalate salt in acetone in 21.3% yield (3.01 g) (softens at 126°–134° C., mp >250° C.).

Theor. $C_{26}H_{37}N_3O_5S \cdot C_2H_2O_4$: C, 56.64; H, 6.62; N, 7.08 Found: C, 56.55; H, 6.81; N, 7.19

EXAMPLE 4

2-[(4-Nitrophenyl)amino]-N-[3-[3-(piperidinomethyl)-phenoxy]propyl]ethanesulfonamide The crude 2-[(4-nitrophenyl)amino]ethanesulfonyl fluoride was produced following the procedure of Example 1 using 4-nitroaniline (6.91 g, 50 mmol) and ethenesulfonyl fluoride (6.06 g, 55 mmol) at 110° C. for three days.

The title compound was produced following the procedure of Example 1 using the above ethanesulfonyl fluoride (9.88 g, 39.5 mmol) and the amine (10.77 g, 43.4 mmol) in Example 1. The title compound was isolated as an orange-yellow oil in 20% yield (3.80 g) after silica gel (200 g) chromatography and was converted to its monooxalate salt in acetone, mp 140°–142° C.

Theor. $C_{23}H_{32}N_4O_5S \cdot C_2H_2O_4$: C, 52.99; H, 6.05; N, 9.89 Found: C, 52.57; H, 6.16; N, 9.85

EXAMPLE 5

2-[(4-Bromophenyl)amino]-N-[3-[3-piperidinomethyl)-phenoxy]propyl]ethanesulfonamide The crude 2-[(4-bromophenyl)amino]ethanesulfonyl fluoride was produced following the procedure of Example 1 using 4-bromoaniline (5.16 g, 30 mmol) and ethenesulfonyl fluoride (33 mmol).

The title compound was produced following the procedure of Example 1 using the above ethanesulfonyl fluoride (8.51 g, 30 mmol) and the amine (8.18 g, 33 mmol) in Example 1. The title compound was purified by flash silica gel (200 g) chromatography and the resulting golden-brown oil was converted to its monooxalate salt in acetone in 5.6% yield (1.0 g), mp 119°–121° C.

Theor. $C_{23}H_{32}BrN_3O_3S \cdot C_2H_2O_4$: C, 49.99; H, 5.71; N, 7.00 Found: C, 50.06; H, 5.80; N, 7.07

EXAMPLE 6

2-(Phenylamino)-N-[3-[3-(piperidinomethyl)-phenoxy]-propyl]ethanesulfonamide The crude 2-(phenylamino)ethanesulfonyl fluoride was produced following the procedure of Example 1 using aniline (2.79 g, 30 mmol) and ethenesulfonyl fluoride (33 mmol).

The title compound was produced following the procedure of Example 1 using the above ethanesulfonyl fluoride (5.76 g, 28.3 mmol) and the amine (7.73 g, 31.2 mmol) in Example 1. The title compound was isolated in 13% yield (1.7 g) after flash silica gel (200 g) chromatography using $CH_2Cl_2/MeOH/NH_4OH$ (96/3.5/0.5), and the resulting yellow gum was converted to its monooxalate salt in acetone, mp 111.5°–115° C.

For $C_{23}H_{33}N_3O_3S \cdot C_2H_2O_4 \cdot \frac{1}{2} H_2O$: Theor.: C, 56.58; H, 6.84; N, 7.92 Found: C, 56.73; H, 6.88; N, 7.60

EXAMPLE 7

2-[[4-(1-Methylethoxy)phenyl]amino]-N-[3-[3-(piperidinomethyl)phenoxy]propyl]ethanesulfonamide The crude 2-[[4-(1-methylethoxy)phenyl]amino]ethanesulfonyl fluoride was produced following the procedure of Example 1 using 4-(1-methylethoxy)aniline (7.30 g, 48 mmol) and ethenesulfonyl fluoride (53 mmol).

The title compound was produced following the procedure of Example 1 using the above ethanesulfonyl fluoride (7.86 g, 30 mmol) and the amine (8.18 g, 33 mmol) in Example 1. The title compound was isolated in 7.2% yield (1.7 g) after flash silica gel (200 g) chromatography using $CH_2Cl_2/MeOH/NH_4OH$ (96/3.5/0.5) and was converted to its monooxalate salt in acetone, mp 110°–122° C.

For $C_{26}H_{39}N_3O_4S \cdot C_2H_2O_4 \cdot \frac{1}{2} H_2O$: Theor.: C, 57.12; H, 7.19; N, 7.14 Found: C, 57.04; H, 7.13; N, 6.90

EXAMPLE 8

2-[(4-Pentoxyphenyl)amino]-N-[3-[3-(piperidinomethyl)phenoxy]propyl]ethanesulfonamide The crude 2-[(4-pentoxyphenyl)amino]ethanesulfonyl fluoride was produced following the procedure of Example 1 using 4-pentoxyaniline (10.4 g, 58.1 mmol) and ethenesulfonyl fluoride (60 mmol).

The title compound was produced following the procedure of Example 1 using the above ethanesulfonyl fluoride (10.71 g, 37 mmol) and the amine (10.0 g, 40.7 mmol) in Example 1. The title compound was isolated in 12% yield (3.5 g) after flash silica gel (200 g) chromatography using $CH_2Cl_2/MeOH/NH_4OH$ (97/2.5/0.5) and was converted to its dioxalate salt in methanol, mp 156.5°–160° C. (dec).

Theor. $C_{28}H_{43}N_3O_4S \cdot 2(C_2H_2O_4)$: C, 55.08; H, 6.79; N, 6.02 Found: C, 55.18; H, 6.89; N, 6.28

When in the above procedure, 4-methoxyaniline or 4-butoxyaniline is used in place of the 4-pentoxyaniline, the corresponding (4-methoxyphenyl)amino or (4-butoxyphenyl)amino derivative is obtained.

EXAMPLE 9

2-[(4-Chloro-3-trifluoromethylphenyl)amino]-N-[3-[3-(piperidinomethyl)phenoxy]propyl]ethanesulfonamide The crude 2-[(4-chloro-3-trifluoromethylphenyl)amino]ethanesulfonyl fluoride was produced following the procedure of Example 1 using 5-amino-2-chlorobenzotrifluoride (4.9 g, 25 mmol) and ethenesulfonyl fluoride (27.5 mmol).

The title compound was produced following the procedure of Example 1 using the above ethanesulfonyl fluoride (7.7 g, 25 mmol) and the amine (7.4 g, 30 mmol) in Example 1. The title compound was isolated in 15% yield (2.0 g) as a yellow gum after flash silica gel (200 g) chromatography and was converted to its monooxalate salt in acetone. This tan solid was recrystallized from acetone/ether, mp 115°–120° C.

For $C_{24}H_{31}ClF_3N_3O_3S \cdot C_2H_2O_4$: Theor.: C, 50.04; H, 5.33; N, 6.73 Found: C, 50.06; H, 5.29; N, 6.64

EXAMPLE 10

2-[(4-Butylphenyl)amino]-N-[3-[3-(piperidinomethyl)phenoxy]propyl]ethanesulfonamide The crude 2-[(4-butylphenyl)amino]ethanesulfonyl fluoride was produced following the procedure of Example 1 using 4-butylaniline (4.5 g, 30 mmol) and ethenesulfonyl fluoride (33 mmol).

The title compound was produced following the procedure of Example 1 using the above ethanesulfonyl fluoride (30 mmol) and the amine (8.1 g, 33 mmol) in Example 1. The title compound was isolated in 20% yield (3.0 g) as a yellow oil after flash silica gel (200 g) chromatography using $CH_2Cl_2$/EtOH/$NH_4OH$ (96/3.5/0.5) and was converted to its dioxalate salt in MeOH/acetone/ether, mp 115°–119° C.

For $C_{27}H_{41}N_3O_3S \cdot 2(C_2H_2O_4)$: Theor.: C, 55.76; H, 6.79; N, 6.29 Found: C, 55.89; H, 6.80; N, 6.35

When in the above procedure, 4-ethylaniline or 4-isopropylaniline is used in place of the 4-butylaniline, the corresponding (4-ethylphenyl)amino or (4-isopropylphenyl)amino derivative is obtained.

EXAMPLE 11

2-[(3,4-Dichlorophenyl)amino]-N-[3-[3-[(4-methylpiperidin-1-yl)methyl]phenoxy]propyl]ethanesulfonamide The title compound was produced following the procedure of Example 1 using the ethanesulfonyl fluoride (3.4 g, 12.5 mmol) of Example 1 and 3-[3-[(4-methylpiperidin-1-yl)methyl]phenoxy]propylamine (3.4 g, 12.9 mmol) at reflux for 20 hours. The title compound was isolated in 66.9% yield (4.3 g) as an orange liquid and was converted to its monooxalate salt in acetone/ether, mp 130°–135° C.

For $C_{24}H_{33}Cl_2N_3O_3S \cdot C_2H_2O_4$: Theor.: C, 51.65; H, 5.84; N, 6.95 Found: C, 51.78; H, 5.90; N, 6.84

When in the above procedure, 3-[3-(pyrrolidinomethyl)phenoxy]propylamine or 3-[3-(piperazinomethyl)phenoxy]propylamine is used, the corresponding 3-[3(pyrrolidinomethyl)phenoxy]propyl or 3-[3-(piperazinomethyl)phenoxy]propyl derivative is obtained.

EXAMPLE 12

Pharmacology of the Ethanesulfonamide Compounds—Rabbit Isolated Parietal Cells

Parietal cells were isolated from the fundic mucosa of rabbit stomachs by a four-stage collagenase digestion process. The supernatant fraction from the last two stages of this process contained the individual parietal cells. This cell suspension was centrifuged and

TABLE 1

| Example (Compound) | $IC_{50}$ Data Against Histamine (H) and dbcAMP | |
|---|---|---|
| | $IC_{50}(H)$ ($\mu M$) | $IC_{50}(dbcAMP)$ ($\mu M$) |
| 1 | 0.37 | 0.13 |
| 2 | 0.92 | 1.82 |
| 3 | 0.39 | 2.30 |
| 4 | 0.12 | 3.70 |
| 5 | 0.37 | 0.86 |
| 6 | 1.0 | 10.0 |
| 7 | 0.84 | 2.0 |
| 8 | 0.33 | 0.37 |
| 9 | 0.16 | 0.31 |
| 10 | 0.28 | 0.23 |
| 11 | 0.058 | 0.46 |

EXAMPLE 13

Inhibition of Gastric Secretion in Rat

Male Charles River rats weighing 150–300 grams were deprived of food but not water for 18–24 hours prior to use. Water was withheld during the experiment. The rats were weighed, anesthetized with ether and the pylorus ligated according to the method Shay, H. et al., *Gastroenterol.* 26, 906 (1954). Test compounds were suspended in a 0.5% aqueous solution of methylcellulose (15 cps) and administered intraduodenally (i.d.) at the time of ligation. The rats were housed two per cage and sacrificed with $CO_2$ four hours after ligation. The stomachs were removed and contents emptied into a graduated centrifuge tube. The tubes were centrifuged, reconstituted in a modified Hank's buffer to contain $2\text{-}3 \times 10^6$ cells/ml. The cells in this suspension were then evaluated for their ability to accumulate $^{14}C$-aminopyrine ($^{14}C$-AP), a weak base which has been shown to accumulate in acidic environments such as the parietal cell. The accumulation is stimulated by histamine and is blocked by $H_2$ antagonists. Accumulation of $^{14}C$-AP is also stimulated by dibutyryl cAMP (dbcAMP). The cells were incubated with $0.5 \times 10^6$ cpm $^{14}C$-AP, with various concentrations of histamine or dbcAMP, $1 \times 10^{-5}$ M isobutylmethylxanthine, and test compound added in a 20 $\mu l$ volume of buffer or dimethylsulfoxide. The flasks were incubated in a shaking water bath at 37° C. Two 0.5 ml aliquots were then taken from each flask and cell pellets were collected by centrifugation. The pellets were solubilized with Protosol (NEN) and radioactivity determined by liquid scintillation spectrometry.

The concentration of compound required to inhibit $^{14}C$-AP accumulation in the stimulated parietal cell by 50% ($IC_{50}$) was determned. Table 1 shows the $IC_{50}$s of the compound of Examples 1–11 above. the volume of gastric juice recorded, and any samples obviously contaminated by feces, food or blood eliminated. A 1 ml aliquot of gastric juice was titrated with 0.1 N NaOH to a pH of 7.0–7.4.

The volume of gastric juice secreted, the acid concentration, and the product of the volume times the concentration, i.e., the total amount of acid secreted, were statistically compared by a student's t-test using the pooled error variance. The in vivo activity of these novel ethanesulfonamides is shown in Table 2.

TABLE 2

Reduction of Gastric Secretion in Rat

| Example (Compound) | % Reduction of Total Acid Output | Dose (MPK) |
|---|---|---|
| 1 | 47.9 | 40 |
| 2 | 22.1 | 40 |
| 3 | 25.6 | 40 |
| 4 | 30.8 | 40 |
| 9 | 24.7 | 40 |
| 10 | 23.3 | 20 |
| 11 | 29.0 | 20 |

What is claimed is:

1. A compound of the formula

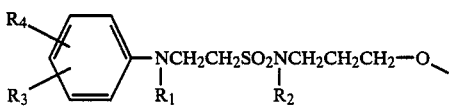

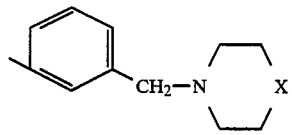

where
R$_1$ is hydrogen or C$_1$–C$_3$ alkyl;
R$_2$ is hydrogen or a pharmaceutically acceptable alkali or alkaline earth metal ion;
R$_3$ is hydrogen, Cl, Br, F, C$_1$–C$_6$ alkyl, C$_3$–C$_6$ branched-chain alkyl, C$_1$–C$_6$ alkoxy, C$_1$–C$_6$ branched-chain alkoxy, CF$_3$, nitro, —NHCOC$_1$–C$_3$ alkyl, NR$_5$R$_6$ or CO$_2$R$_7$ when R$_4$ is hydrogen, or R$_3$ and R$_4$ are the same or different and are Cl, Br, F or CF$_3$;
R$_5$ and R$_6$ are the same or different and are hydrogen or C$_1$–C$_3$ alkyl;
R$_7$ is hydrogen or C$_1$–C$_6$ alkyl;
X is O, NR$_8$, CHR$_8$ or —(CH$_2$)$_n$—;
R$_8$ is C$_1$–C$_3$ alkyl; and
n is 0, 1, 2 or 3;
and its physiologically acceptable salts.

2. The compound of claim 1 wherein R$_1$, R$_2$ and R$_4$ are hydrogen; R$_3$ is hydrogen, Cl, Br, F, nitro, C$_1$–C$_6$ alkyl, C$_3$–C$_6$ branched-chain alkyl, CF$_3$ or CO$_2$R$_7$; R$_7$ is C$_1$–C$_6$ alkyl; X is —(CH$_2$)$_n$—, and n is 1 or 2.

3. The compound of claim 1 wherein R$_1$ and R$_2$ are hydrogen; R$_3$ and R$_4$ are the same or different and are Cl or CF$_3$; X is —(CH$_2$)$_n$—, and n is 1 or 2.

4. The compound of claim 1 selected from the group consisting of 2-[(4-fluorophenyl)amino]-N-[3-[3-(piperidinomethyl)phenoxy]propyl]ethanesulfonamide, 2-[(4-ethoxycarbonylphenyl)amino]-N-[3-[3-piperidinomethyl)phenoxy]propyl]ethanesulfonamide, 2-[(4-nitrophenyl)amino]-N-[3-[3-(piperidinomethyl)-phenoxy]propyl]ethanesulfonamide, 2-[(4-bromophenyl)amino]-N-[3-[3-piperidinomethyl)phenoxy]-propyl]ethanesulfonamide, 2-(phenylamino)-N-[3-[3-(piperidinomethyl)phenoxy]propyl]ethanesulfonamide, 2-[[4-(1-methylethoxy)phenyl]amino]-N-[3-[3-(piperidinomethyl)phenoxy]propyl]ethanesulfonamide, 2-[(4-pentoxyphenyl)amino]-N-[-3-[3-(piperidinomethyl)phenoxy]propyl]ethanesulfonamide, and 2-[(4-butylphenyl)amino]-N-[-3-[3-(piperidinomethyl)-phenoxy]propyl]ethanesulfonamide.

5. The compound of claim 1 selected from the group consisting of 2-[(3,4-dichlorophenyl)amino]-N-[3-[-3-piperidinomethyl)phenoxy]propyl]ethanesulfonamide, 2-[(4-chloro-3-trifluoromethylphenyl)amino]-N-[3-]3-(piperidinomethyl)phenoxy]propyl]ethanesulfonamide, and 2-[(4-butylphenyl)amino]-N-[3-[3-(piperidinomethyl)phenoxy]propyl]ethanesulfonamide.

6. A pharmaceutical composition comprising an effective amount of a compound of claim 1 and a pharmaceutically acceptable carrier.

7. A method for treating peptic ulcer disease of a mammal which comprises administering to a mammal an effective amount of a compound of the formula

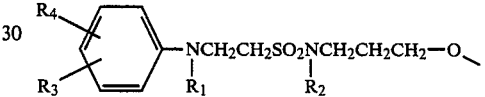

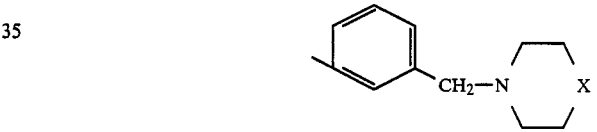

where
R$_1$ is hydrogen or C$_1$–C$_3$ alkyl;
R$_2$ is hydrogen or a pharmaceutically acceptable alkali or alkaline earth metal ion;
R$_3$ is hydrogen, Cl, Br, F, C$_1$–C$_6$ alkyl, C$_3$–C$_6$ branched-chain alkyl, C$_1$–C$_6$ alkoxy, C$_3$–C$_6$ branched-chain alkoxy, CF$_3$, nitro, —NHCOC$_1$–C$_3$ alkyl, NR$_5$R$_6$ or CO$_2$R$_7$ when R$_4$ is hydrogen, or R$_3$ and R$_4$ are the same or different and are Cl, Br, F or CF$_3$;
R$_5$ and R$_6$ are the same or different and are hydrogen or C$_1$–C$_3$ alkyl;
R$_7$ is hydrogen or C$_1$–C$_6$ alkyl;
X is O, NR$_8$, CHR$_8$ or —(CH$_2$)$_n$—;
R$_8$ is C$_1$–C$_3$ alkyl; and
n is 0, 1, 2 or 3;
and its physiologically acceptable salts.

* * * * *

UNITED STATES PATENT AND TRADEMARK OFFICE
CERTIFICATE OF CORRECTION

PATENT NO. : 4,874,771

DATED : October 17, 1989

INVENTOR(S) : Ronald K. Russell

It is certified that error appears in the above-identified patent and that said Letters Patent is hereby corrected as shown below:

Claim 1, Column 9, Line 37 "$C_1$-$C_6$ alkoxy, $C_1$-$C_6$" should be --$C_1$-$C_6$ alkoxy, $C_3$-$C_6$--.

Claim 1, Column 9, Line 38 "-NHCOC-" should be -- -NHCOC$_1$ --.

Claim 1, Column 9, Line 39 delete "1" at the beginning of the sentence.

Signed and Sealed this

Eighteenth Day of December, 1990

Attest:

HARRY F. MANBECK, JR.

*Attesting Officer*  *Commissioner of Patents and Trademarks*